United States Patent [19]

Strobel

[11] 3,995,034

[45] Nov. 30, 1976

[54] BIOCIDAL 3,5-DIBROMOSALICYLIC ACID SALTS

[75] Inventor: Albert F. Strobel, Delmar, N.Y.

[73] Assignee: GAF Corporation, New York, N.Y.

[22] Filed: Oct. 3, 1975

[21] Appl. No.: 619,184

Related U.S. Application Data

[63] Continuation of Ser. No. 453,539, March 21, 1974, abandoned, which is a continuation of Ser. No. 186,506, Oct. 4, 1971, abandoned.

[52] U.S. Cl. .............................................. 424/231
[51] Int. Cl.² ....................... A01N 9/02; A01N 9/24
[58] Field of Search ............................ 424/294, 231

[56] References Cited
FOREIGN PATENTS OR APPLICATIONS 6,414,686  6/1965  Netherlands

OTHER PUBLICATIONS

DeLauney, Chem. Abst. vol. 31, (1937), p. 8599.
Chem. Abst. 7th Coll. Index vol. 56-65, (1962-1966 sub. PS-SN p. 26.
Hirwe et al., Chem. Abst. vol. 31 (1937), p. 6215.
Gershon et al., Appl. Microbiol. 10, 348-353 (1962).
Rochaix et al., Chem. Abst. vol. 22, (1928), p. 443.
The Merck Index, (1960), p. 304.

Primary Examiner—James O. Thomas, Jr.
Assistant Examiner—Allen J. Robinson
Attorney, Agent, or Firm—Walter C. Kehm; James N. Blauvelt

[57] ABSTRACT

Biocides which have fungicidal and bactericidal activity are metal salts of 3,5-dibromosalicylic acid of the following formula:

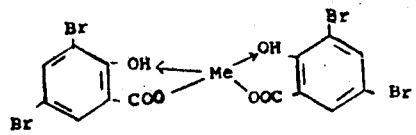

wherein Me is a divalent metal such as copper.

3 Claims, No Drawings

BIOCIDAL 3,5-DIBROMOSALICYLIC ACID SALTS

CROSS-REFERENCE TO RELATED APPLICATIONS

This application is a continuation of application Ser. No. 453,539, filed Mar. 21, 1974, now abandoned, which was a continuation of U.S. Ser. No. 186,506, filed Oct. 4, 1971, and now also abandoned.

BACKGROUND OF THE INVENTION

1. Field of the Invention

This invention relates to salts of 3,5-dibromosalicyclic acid and more particularly to metal salts of 3,5-dibromosalicylic acids which have excellent fungicidal and bactericidal activity.

2. Description of the Prior Art

The compound, 3,5-dibromosalicylic acid, is known in the art per se and has been described as having bactericidal action as may be seen, for example in the Bull. des Sciences Pharmacologiques, 34, 486–7(1927), Chem. Abs., 22, 443, (1928), for use in a disinfectant cleaning composition as shown in Netherlands Application No. 6,414,686 as well as a growth regulant in Botannical Gazette 113, 135–147 (1951). In addition Beilstein, 10, p. 109 describes the barium and lead salts of 3,5 dibromosalicylic acid and Proc. Ind. Acad. Sci. 5A, 321–5(1937), abstracted Chem. Abs., 31, 6215, describe the Na, K and Ca salts of 3,5-dibromosalicylic acid.

However, it has not been known heretofore that salts of 3,5-dibromosalicylic acid possess biocidal activity can be particularly useful as fungicides and bactericides. It was surprisingly discovered that the metal salts of 3,5-dibromosalicylic acid have substantially higher biocidal action, e.g. as fungicides, than the corresponding free acids and also exhibit greater mildew growth retardation than the free acids.

SUMMARY OF THE INVENTION

It is accordingly one object of the present invention to provide biocidally-active salts of 3,5-dibromosalicylic acid.

A further object of the invention is to provide metal salts of 3,5-dibromosalicylic acid which have excellent fungicidal and bactericidal activity and also exhibit mildew growth retarding action.

A still further object of the invention is to provide metallic salts of 3,5-dibromosalicylic acid which have fungicidal and bactericidal activity, processes for preparation of these compounds and compositions and methods of use of these compounds in fungicidal and bactericidal applications.

Further objects and advantages of the present invention will become apparent as the description thereof proceeds.

In satisfaction of the foregoing objects and advantages there is provided by this invention metal salts of 3,5-dibromosalicylic acid which exhibit superior activity as fungicides and bactericides. These metallic salts may be characterized by the following general structural formula:

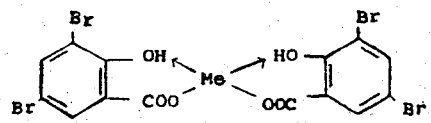

wherein Me is a divalent metal such as copper. Also provided are methods for preparation of these compounds, biocidal compositions and methods of use in the fungicidal and bactericidal areas.

DESCRIPTION OF THE PREFERRED EMBODIMENTS

As pointed out above this invention is concerned with a certain metallic salt of 3,5-dibromosalicylic acid which has been found to exhibit superior fungicidal and bactericidal activity over the corresponding free acids. In addition, this product has been found to have greater mildew growth-retarding action both in the presence and absence of light than the correspondingly free acid or the commercial product 3,4',5-tribromosalicylanilide, even when both compounds are employed in a detergent bath in the presence of hypochlorite. The metallic salts of this invention are of the following structural formula:

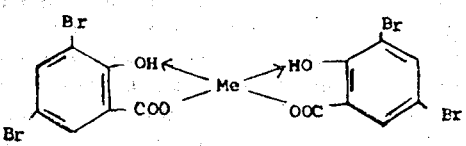

wherein Me is a divalent metal of copper.

In the above formula, while the majority of the products are believed to be connected to the divalent metal through the carboxylic acid groups, the structural formula is written to indicate that the compound may also contain tautomeric forms wherein the metal may be connected to either or both the carboxylic acid and the hydroxyl group in the ortho position. Therefore, it is to be understood that any or all of the possible products are intended to be included by this structural formula.

The invention of this application is primarily concerned with compositions for, and methods for use of, the copper metal salts in bactericidal and fungicidal applications.

The products of this invention are conveniently prepared by reaction of the 3,5-dibromosalicylic acid in water solution with the salt of the desired copper metal. Preferably, the water solution of the salicylic acid is rendered basic prior to reaction with the metallic salt. Preferred procedures for obtaining the basic solution is by dissolving the salicylic acid starting material in water and adding an alkali metal salt such as sodium carbonate, sodium bicarbonate and the like, in order to initially form the sodium salt of the salicylic acid and then exchanging the sodium salt with the divalent metal of copper which is added in the form of a water soluble salt. Addition of the copper metal salt and heating the mixture at about 50°–100°C., cooling, filtering, washing and drying will provide the preferred product of the invention. It is highly preferred that the metallic salt be added in the form of its chloride such as cupric chloride, although other suitable water soluble salts of this metal may be used as desired.

In use as bactericides and fungicides, the products of this invention may be employed with a carrier such as by forming a dispersion in water with, for example dimethylformamide, in an amount of about 0.01 to 5 weight percent of the compound per weight of the carrier. The resulting composition may be applied as a fungicide or bactericide in known manner. To be effective, about 0.01 to 1.0 wt. % of the active compound per weight of the carrier is applied to the bacteria or fungi.

The products of this invention are effective in the protection of textiles, wood, paper and other cellulosic fibrous materials from the deleterious action of fungi and other cellulose destroying organisms. They may be applied in general for the finishing of textiles to reduce mildew deterioration. They may be applied to the foliage of trees and plants for fungus control, in washing apples and oranges and the like, for the inhibition of pathogens, for treating seeds, for the drenching of flats of seedlings and for the prevention of damp-off.

The preservatives may be modified by the addition thereto of adjuvants, such as wetting agents, water repellants, insect repellants, fire retardants, substances which have a synergistic action, or have a desirable action in further protecting or enhancing the value of the treated article.

The carrier employed is a selective material or materials into which the compounds of this invention are incorporated to produce the fungicidal or bactericidal compositions. Since these compounds are water soluble, water is the preferred carrier, but any carrier, such as a solvent in which the compounds are soluble or dispersible, dust, or other material chosen for a particular intended use of the toxicant incorporated therein, may be employed.

The following examples are presented to illustrate the invention but it is not to be considered as limited thereto. Unless otherwise indicated the parts are by weight in the following examples.

EXAMPLE 1

To 10 gms. of 3,5-dibromosalicylic acid in 100 ml. water is added 17 ml. $Na_2CO_3$ (20% soln., wt./vol.) until phenolphthalein pink is obtained. To this solution is then added 10 gms. $CuCl_2$ in 5 ml. water. The mixture is heated 1 hour at 70° C., cooled, filtered, washed and dried to give a product having the following formula:

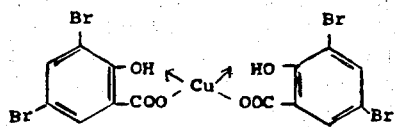

A dispersion is made by treating 0.1 gm. of this product with 2 ml. dimethylformamide at 70° C. and drowning into 100 ml. water. The calculated fraction is taken and diluted with water to give 25 ppm of compound. A 1½ inch square piece of Whatman paper No. 2 is dipped into the solution, allowed to dry, then maintained under sterile conditions at 80° F.

A culture medium is then prepared consisting of:

| Component | gms. |
|---|---|
| ammonium nitrate | 3.0 |
| potassium monohydrate orthophosphate | 2.5 |
| magnesium sulfate; $7H_2O$ | 2.0 |
| agar | 20.0 |
| distilled water, up to | 1000.00 |

The pH is adjusted to 6.4–6.8 and the solution is sterilized in an autoclave for 20 minutes at 250° F. and 15 lbs. pressure, and then cooled.

A Petri dish which had been innoculated with chaetomium globosum and incubated for 10 days is scraped and stirred into a flask containing 100 ml. of distilled water. A transfer loop is employed to admix the chaetomium globosum with the culture medium.

The paper treated as described above and an untreated piece are dipped into the inoculated culture medium and then maintained under sterile conditions at 80° F. After 24, 48 and 72 hours the paper treated with the compound showed much less growth of mildew than the untreated paper.

The invention has been described herein with reference to certain preferred embodiments. However, as obvious variations thereon will become obvious to those skilled in the art the invention is not to be considered as limited thereto.

What is claimed is:

1. An aqueous fungicidal or bactericidal dispersion comprising water, a water-miscible carrier, and a fungicidally or bactericidally effective amount of a metallic salt of a 3,5-dibromosalicylic acid of the following formula:

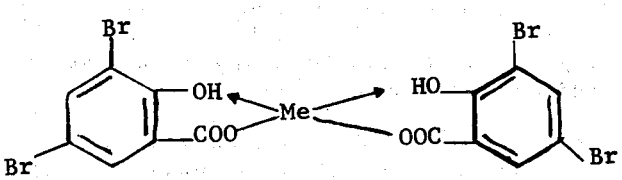

wherein Me is a divalent metal of copper.

2. The dispersion according to claim 1, wherein the water-miscible carrier is dimethylformamide.

3. A method of destroying fungal or bacterial organisms, comprising applying to said organisms to be destroyed a fungicidal or bactericidal amount of the dispersion as defined in claim 1.

* * * * *